United States Patent
Tamura et al.

[19]

[11] Patent Number: 6,143,258
[45] Date of Patent: *Nov. 7, 2000

[54] APPARATUS FOR DISPENSING DRINKING WATER

[75] Inventors: Shigeki Tamura, Ikeda; Hiroaki Kitamura, Nishinomiya; Shinichi Kunisaki, Ibaraki; Nobuya Matsumoto, Osaka, all of Japan

[73] Assignee: Suntory Limited, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/804,232

[22] Filed: Feb. 21, 1997

Related U.S. Application Data

[63] Continuation of application No. 08/644,715, May 10, 1996, abandoned, which is a continuation of application No. 08/509,416, Jul. 31, 1995, abandoned, which is a continuation of application No. 08/280,144, Jul. 25, 1994, abandoned, which is a continuation of application No. 08/096,462, Jul. 22, 1993, abandoned.

[30] Foreign Application Priority Data

Jul. 24, 1992 [JP] Japan .................................. 4-197924

[51] Int. Cl.[7] .................................................. B01D 35/18
[52] U.S. Cl. ........................ 422/307; 210/175; 210/416.3; 422/308
[58] Field of Search ................................ 422/40, 43, 307, 422/308, 905; 222/146.1, 146.3, 146.6, 148; 210/175, 416.3, 742

[56] References Cited

U.S. PATENT DOCUMENTS

| | | | |
|---|---|---|---|
| 3,069,735 | 12/1962 | Toulmin, Jr. | 422/307 |
| 3,698,603 | 10/1972 | Radcliffe | 222/146.1 |
| 3,733,840 | 5/1973 | Pearl et al. | 222/148 X |
| 4,207,994 | 6/1980 | Offlee, Sr. | 222/146.1 |
| 4,792,059 | 12/1988 | Kerner et al. | 222/146.1 X |
| 5,139,676 | 8/1992 | Ebisawa et al. | 210/651 |

FOREIGN PATENT DOCUMENTS

| | | | |
|---|---|---|---|
| 420009 | 5/1991 | European Pat. Off. | 422/308 |

*Primary Examiner*—Krisanne Thornton
*Attorney, Agent, or Firm*—Bachman & LaPointe, P.C.

[57] ABSTRACT

An apparatus for dispensing drinking water including of a chamber in which a container packed with drinking water is mounted, a conduit connected with the container in the chamber to dispense drinking water through the apparatus, and sterilizer installed adjacent the conduit means to apply sterilization with substantial heat thereto. The sterilizing means may include automatic control system to control automatically sterilizing with heat. The conduit may includes a storage area for storing drinking water within the conduit, and the storage area may includes two tanks for storing drinking water, one is a cold water tank including a refrigeration device to chill the drinking water, and the other is a hot water tank including heating device to heat the drinking water. The sterilization with heat may be done by heating the conduit with heaters installed surrounding thereof, or may be done by circulating hot water which is stored in the hot water tank through the apparatus. Furthermore, the sterilizer installed adjacent said conduit with the exception of the portions in which hot water is usually passed through in the apparatus during dispensing the drinking water to apply substantial sterilization with heat thereto.

12 Claims, 2 Drawing Sheets

APPARATUS FOR DISPENSING DRINKING WATER

This is a continuation of application Ser. No. 08/644,715 filed on May 10, 1996, now abandoned, which is a continuation of application Ser. No. 08/509,416 filed on Jul. 31, 1995, now abandoned which is a Continuation of application Ser. No. 08/280,144, filed Jul. 25, 1994, now abandoned which is a Continuation of application Ser. No. 08/096,462, filed Jul. 22, 1993, now abandoned.

BACKGROUND OF THE INVENTION

1. Field of the Invention

The present invention relates generally to an apparatus for dispensing drinking water. Specifically, the present invention relates to such apparatus having sterilization means installed therein.

2. Description of the Background Art

Generally, in an apparatus for dispensing drinking water, various bacteria are multiplied in the drinking water stored in the apparatus for a long time, especially when no drinking water is dispensed from the apparatus for a long time because the water is retained in conduit means of the apparatus. Therefore, the apparatus has been sterilized by introducing bactericides or hot water thereinto. Alternatively, a filtration system for removing bacteria can be installed in the apparatus. When city water is utilized in the apparatus for the dispensing water, bacterial pollution does not significantly occur because the city water is preliminarily sterilized by chlorine and the chlorine keeps the water sterilized. However, when natural water or mineral water is utilized in the apparatus for the dispensing water, such water is severely suffers from bacterial pollution.

The conventional sterilization, such as introducing bactericides or hot water into the apparatus, requires supply means for supplying bactericides or hot water to the apparatus, and drain means for draining those from the apparatus. Such supply and drain means become external means to be connected with the apparatus. Therefore, connection and operation of such external means are very complicated causing labor intensity and time consumption to be increased. If the supply and drain means are installed within the apparatus, the apparatus becomes too large to easily mount and operate. Furthermore, when the filtration system is installed in the apparatus, bacteria tend to be retained on the filtration system and to be significantly multiplied therein. Therefore, the filtration system must be frequently replaced or cleaned up.

SUMMARY OF THE INVENTION

It is therefore a principal object of the present invention to provide an apparatus for dispensing drinking water in which sterilization means is installed.

It is another object of the present invention to provide an apparatus for dispensing sanitary drinking water including sterilization means which is easily and simply operated.

It is a furthermore object of the present invention to provide an apparatus for dispensing drinking water of a smaller size even though sterilization means is installed therein.

It is additional object of the present invention to make sterilizing condition of drinking water in an apparatus for dispensing drinking water clear and provide efficient sterilizing method of drinking water in the apparatus for dispensing drinking water.

In order to accomplish the aforementioned and other objects, an apparatus for dispensing drinking water is composed of a chamber in which a container packed with drinking water is mounted, conduit means connected with the container to dispense drinking water through the apparatus, sterilizing means installed adjacent the conduit means to apply sterilization with substantial heat thereto. Storage means for storing drinking water within the conduit means may be comprised in the conduit means.

The storage means may include two tanks for storing drinking water, one is a cold water tank including refrigeration means to chill the drinking water, and the other is a hot water tank including heating means to heat the drinking water.

The sterilizing means may include automatic control system to control automatically operation of sterilizing with heat.

Conditions of applying sterilization with heat to said apparatus may be determined on the basis of the following formula:

$$10^{-|(T-55)/5|} \times 5 = t(\min.)$$

wherein T(° C.) is the temperature of the apparatus and t(min.) is sterilization time passed after temperature of the apparatus reaches T. T is determined at more than 49° C.

The sterilizing means may include plurality of heaters installed surrounding the conduit means.

Alternatively, the sterilizing means may include hot water circulating means to circulate hot water through the apparatus.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENT

Figure 1:
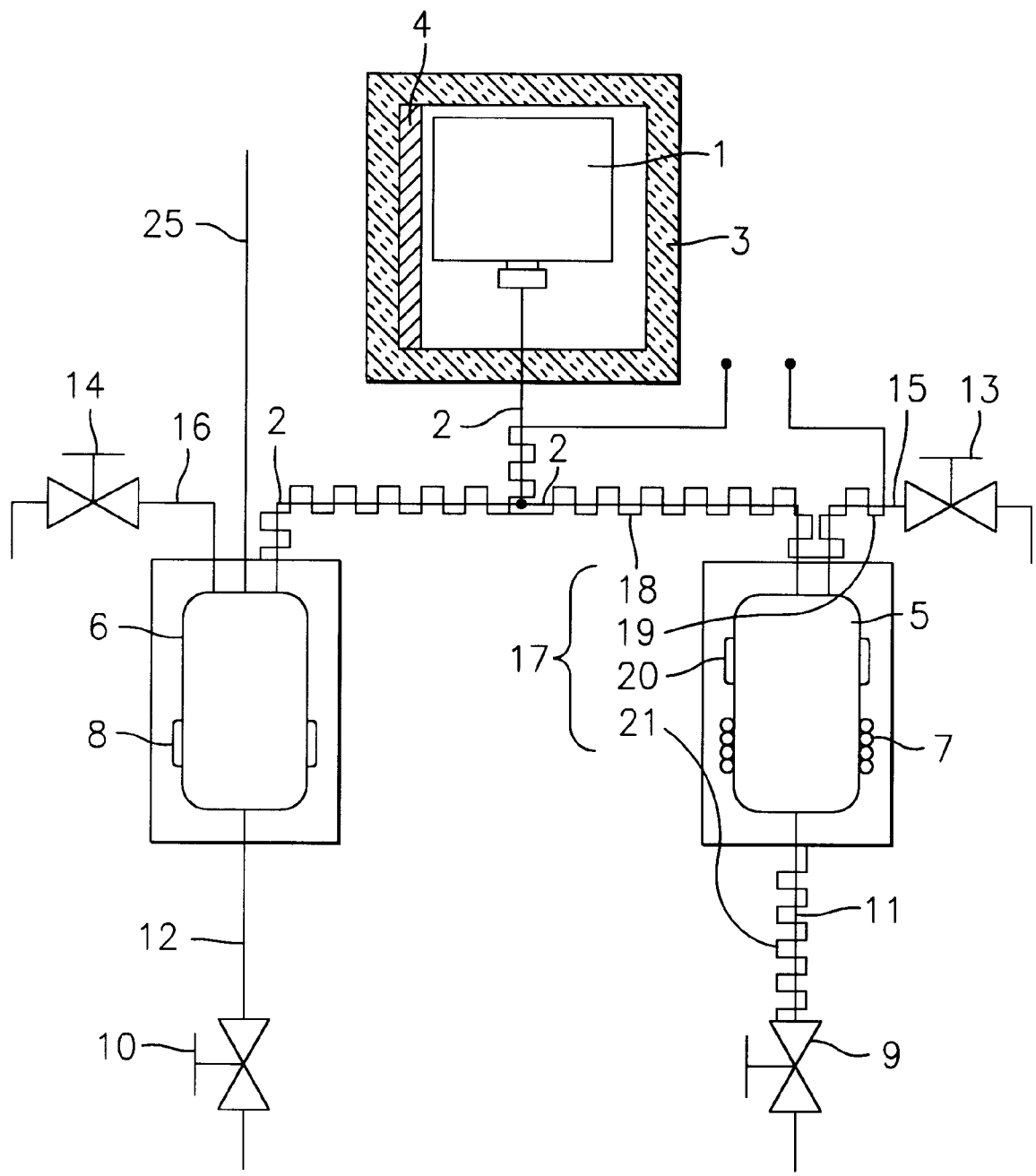
FIG. 1 is a schematic view showing a structure of an apparatus for dispensing drinking water having conduit means according to a first embodiment of the present invention.

Referring now to the drawings, particularly to FIG. 1, a schematic view of an apparatus for dispensing drinking water according to a first embodiment of the present invention is shown. A container 1 of bag-in-box type includes an inner bag filled with drinking water and a discharge tube extended therefrom. The inner bag of the container 1 is joined to a supply conduit 2 via the discharge tube. Any containers having sealability may be suitable for the drinking water container. For example, when a bag-in-box type container having a spout attached to the inner bag is used, the spout of the container can connect with the supply conduit 2 via connecting accessory. If the bag-in-box type container 1, as illustrated in FIG. 1, including the discharge tube is used, the container joins to the supply conduit 2 via the discharge tube simply without any additional means, in addition, bacterial pollution of the apparatus especially the connecting part can be previously prevented.

The container 1 is installed in a chamber 3 having refrigeration means 4 installed therein to chill the drinking water in the container 1 to about 4 to 10° C. Bacteria are not easily multiplied in the drinking water of the container 1, if it will be stored at low temperatures. A check valve may be installed at connecting part of the container 1 and the supply conduit 2 to prevent back flow of drinking water from the apparatus toward the container 1. If bacterial pollution of drinking water in the apparatus occurs, incursion of bacteria from the apparatus into the container 1 can also be prevented.

The drinking water discharged from the discharge tube of the container 1 naturally falls and flows into the supply conduit 2. The inner bag of the container 1 may be pressurized to discharge the water from the container 1. Usage of a pump for discharging is also available.

The water which is flowed into the supply conduit 2 is individually stored in a cold water tank 5 and a hot water tank 6. The water is chilled to the temperatures about around 4 to 10° C. in the cold water tank 5 by refrigeration means 7 equipped therewith. On the other hand, the temperature of the water is maintained about around 80 to 90° C. in the hot water tank 6 by means of a heater 8 with thermostat equipped with the hot water tank 6. Drain valves 9 and 10 are respectively installed to each tanks 5 and 6 via drain conduits 11 and 12. A steam outlet pipe 25 is connected with the hot water tank 6 to exhaust steam in the hot water tank 6 toward the outside of the apparatus.

The water respectively stored in the cold water tank 5 and the hot water tank 6 are discharged therefrom by a cold water discharge valve 13 or a hot water discharge valve 14 via a discharge conduit 15 or 16, respectively.

In a first embodiment of the present invention, heat sterilizing means 17 including sterilizing heaters 18, 19, 20 and 21 is installed in the apparatus. A sterilizing heater 18 is installed adjacent said supply conduit 2, a sterilizing heater 19 is installed adjacent said discharge conduit 15 from a cold water tank 5, a sterilizing heater 20 is installed adjacent said a cold water tank 5 and a sterilizing heater 21 is installed adjacent said drain conduit 11 from a cold water tank 5. The operation of refrigeration means 7 of the cold water tank 5 is shutdown before starting the sterilizing operation. Then, the heaters 18, 19 and 20, having thermostat so as not to heat to above the temperature required for sterilization, are operated. Alternatively, instead of equipment of the heater 21, the hot water obtained from heating the water in the cold water tank 5 by the heater 20 may be passed through the drain conduit 11. Sterilizing conditions are preferably determined on the basis of the following formula, wherein T(° C.) is the temperature of the apparatus and t(min.) is the sterilizing time passed after the temperature is raised to T. Here, T is determined at more than 49° C.

$$10^{-|(T-55)/5|} \times 5 = t(\text{min.})$$

For example, when the temperature T is determined at 55° C., about 5 min. of sterilization is enough.

In the first embodiment, sterilizing heater is not arranged to the hot water tank 6 and conduit means therearound. The temperature of the water in the hot water tank 6 is usually maintained to about 80 to 90° C. as previously mentioned, therefore, the hot water tank 6, the drain valve 10, the drain conduit 12, the discharge conduit 16, and the discharge valve 14 are always sterilized by the hot water. Accordingly, excessive arrangement of sterilizing means is not necessary. However, the arrangement of the sterilizing means depends on the temperature of the drinking water in the hot water tank, and the structure of the apparatus.

When the heat sterilization is finished, the operation of the sterilizing heaters 17 is shutdown, then the refrigeration means 7 installed to the cold water tank 5 is operated. The drinking water in the hot water tank 6 can be rightly prepared at the suitable temperatures of about 80 to 90° C. On the other hand, the cold water at the suitable temperatures of 4 to 10° C. is obtained after 1 to 2 hours when the refrigerating operation is started. Time for chilling the water depends on the capacity of the refrigeration means.

Figure 2:
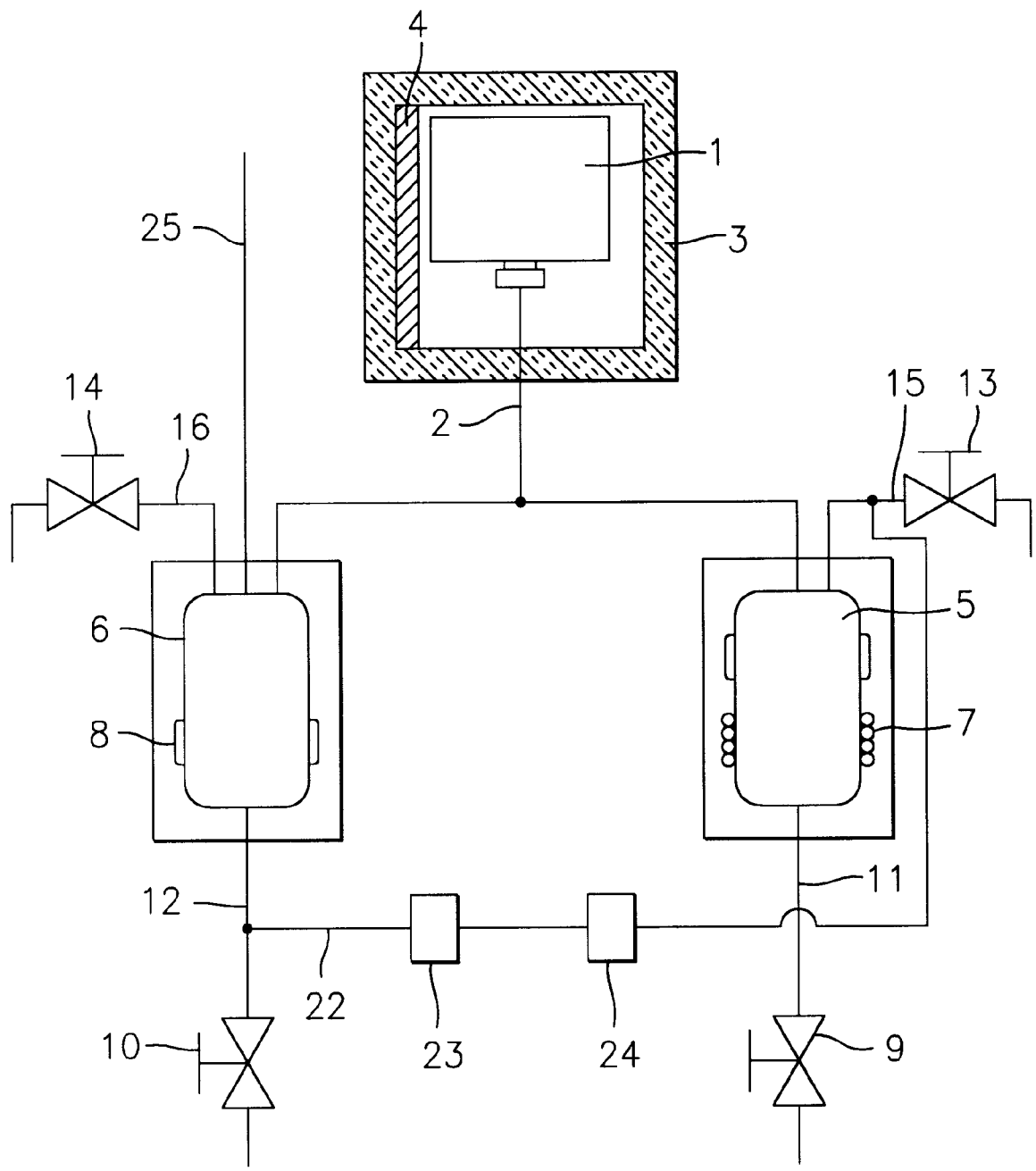
FIG. 2 is a schematic view showing a structure of an apparatus for dispensing drinking water having conduit means according to a second embodiment of the present invention.

Referring now to FIG. 2, showing a second embodiment of the present invention, sterilization is done by circulation hot water through an apparatus for dispensing drinking water. A schematic structure of the apparatus is identical with that of the first embodiment. The portions of the second embodiment identically with those of the first embodiment are designated by the same numerals to omit the repetitive description. Conduit means 22 for circulating hot water in the apparatus is installed instead of the heaters 17 of the first embodiment.

The conduit means 22 communicates to between the drain conduit 12 of the hot water tank 6 and the discharge conduit 15 for discharging the cold water from the cold water tank 5. A circulating pump 23 to circulate the hot water for sterilization and a shut-off valve 24 are arranged in the course of the conduit means 22. The shut-off valve 24 is usually closed but opened when sterilization is required to begin communication of the hot water therethrough. The water may be alternatively supplied from the container 1 to both of the hot water tank 6 and the cold water tank 5 during ordinary dispensing the drinking water, and not supplied from the container 1 to both of tanks during sterilization of the apparatus by arranging a valve at a junction of the supply conduit 2. Alternatively, the apparatus may be designed so that the hot water for sterilization is not flow back to the container 1.

The apparatus of the second embodiment is sterilized by circulating the hot water in the hot water tank 6 through the apparatus. The hot water in the hot water tank 6 is maintained at the temperatures about 80 to 90° C. by the heater 8 with the thermostat. Therefore, the hot water in the hot water tank 6 can be utilized for dispensing and sterilizing.

The operation of the refrigeration means 7 installed in the cold water tank 5 is shutdown. Then, the shut-off valve 24 arranged in the midway of the conduit means 22 is opened to begin communicating the conduit means 22. The hot water in the hot water tank 6 is circulated by the circulating pump 23 through the apparatus. The hot water is introduced into the conduit means 22 via the portion of the drain conduit 12 toward the drain valve 10, then flowed into the discharge conduit 15 toward the discharge valve 13. The drain valve 10, the drain conduit 12, the discharge conduit 15 and the discharge valve 13 can be sterilized by circulation of the hot water. The hot water flowed into the discharge conduit 15 is then flowed into the cold water tank 5, and flowed back to the hot water tank 6 via the supply conduit 2. Thus, the cold water tank 5 and the supply conduit 2 can be sterilized by the circulation of the hot water. The circulation of the hot water is preferably done under conditions defined by the following formula, wherein T(° C.) is the temperature of the apparatus and t(min.) is the sterilizing time passed after the temperature is raised to T. Here, T is determined at more than 49° C.

$$10^{-|(T-55)/5|} \times 5 = t(\text{min.})$$

When the heat sterilization is finished, the shut-off valve 24 is closed to stop communicating the conduit mean 22 and the operation of the circulating pump 23 is shutdown. Then, the refrigeration means 7 installed in the cold water tank 5 is operated. The water in the hot water tank 6 can be rightly prepared at the suitable temperatures of about 80 to 90° C. On the other hand, the cold water at the suitable temperatures of 4 to 10° C. is obtained after 1 to 2 hours when the refrigerating operation is started. Time for chilling the water depends on the capacity of the refrigeration means.

In the both embodiments, central processing unit (CPU) system, not illustrated in the figures, are installed to automatically control the operations of the heat sterilizing means 17, the circulating pump 23, the shut-off valve 24 and other operations for sterilization. The sterilizing operation may be started under control of the CPU when dispensing of the drinking water is not required. Automatically operation of the sterilization may also be done by the CPU. Installation of a timer may be preferable. Thus, the sterilizing operation can be effectively done to smoothly prepare the cold water for being suitable.

In order to define the preferable sterilization conditions, the following experiments were done using *Pseudomonas paucimobilis* and Coryneform group which have been well known as bacteria found in the drinking water.

*Pseudomonas paucimobilis* and Coryneform group were cultivated on SMA medium at 27° C. for 5 days. Then, one colony of each bacteria was respectively sampled to suspend in 10 ml of natural water (traded by Suntory Limited in the trade name of "Natural mineral water from the southern Alpe."). Number of each bacteria in each one colony was about $10^7$/ml. The obtained suspension was diluted by said natural water to the concentration in which about $10^2$/ml of bacteria being cultivated. Then, the obtained solution was cultivated at 27° C. for 5 days. After cultivation, 100 µl of the solution was added to a PET bottle including 1.5 l of said natural water. The solution in the PET bottle was stored at 27° C. for 1 week to prepare a culture solution. 10 ml of the culture solution were pipetted into the plurality of test tubes to place in thermostatic bath of which temperatures were respectively maintained at 50° C., 55° C. and 60° C. The culture solutions in the test tubes were heated in each thermostatic bath to the temperatures which are regulated in each thermostatic bath and the temperatures were maintained. Each test tube was taken out from the respective thermostatic bath when 5, 10, 20, 30 and 60 min. were passed after the temperature of the culture solution reaches to the regulated temperature in each thermostatic bath, then rapidly cooled by iced water. The cooled solution was diluted from 100 µl thereof was spread on SMA medium, cultivated at 27° C. for 5 days. Number of colony was measured. On the other hand, 100 µl of the culture solution was added to a PET bottle including the natural water (not heated) then cultivated at 27° C. for 1 week to prepare a control solution.

The obtained results are shown in Tables 1 and 2.

TABLE 1

Heat resistance of *Pseudomonas paucimobilis*

| T | Control | 0 min. | 5 min. | 10 min. | 20 min. | 30 min. | 60 min. |
|---|---|---|---|---|---|---|---|
| 50° C. | $4.6 \times 10^4$ | $2.5 \times 10^3$ | $1.8 \times 10^3$ | $1.6 \times 10^3$ | $8.6 \times 10^2$ | $4.3 \times 10^1$ | 0 |
| 55° C. | $4.6 \times 10^4$ | $3.4 \times 10^2$ | 0 | 0 | 0 | 0 | 0 |
| 60° C. | $4.6 \times 10^4$ | 0 | 0 | 0 | 0 | 0 | 0 |

TABLE 2

Heat resistance of *Coryneform group*

| T | Control | 0 min. | 5 min. | 10 min. | 20 min. | 30 min. | 60 min. |
|---|---|---|---|---|---|---|---|
| 50° C. | $4.1 \times 10^3$ | $8.7 \times 10^2$ | $5.9 \times 10^2$ | $3.7 \times 10^3$ | $7.4 \times 10^1$ | 0 | 0 |
| 55° C. | $4.1 \times 10^3$ | $2.1 \times 10^2$ | 0 | 0 | 0 | 0 | 0 |
| 60° C. | $4.6 \times 10^3$ | 0 | 0 | 0 | 0 | 0 | 0 |

Accordingly, we have found a relationship between the temperature T(° C.) of the apparatus (temperature of the thermostatic bath) and the time t(min.) for sterilization after the water reaches to the temperature T. The relationship therebetween is defined by the following formula.

$$10^{-|(T-55)/5|} \times 5 = t(\text{min.})$$

Here, as is clearly understood from the above-mentioned formula and the results shown in the aforementioned tables. The temperature T is determined at more than 49° C.

According to the present invention, the portions where bacteria may be multipliable in the apparatus for dispensing drinking water can be thoroughly sterilized by installing heat sterilization means to sterilize the conduits. The heat sterilization can be done by heating the conduit means and the storage means with heaters installed surrounding thereof. Also the heat sterilization can be done by circulating hot water which is stored in the hot water tank through the apparatus. Furthermore, it may be omitted to heat or circulate hot water for the hot water tank and their surrounding conduits as the portions in which hot water is usually passed through. Sterilization can be effectively and simply done to always dispensing the sanitary drinking water. Moreover, the sterilization of the present invention can be easily done by automatic control system. Therefore, time and labor for sterilization can be saved. Further to say, the apparatus of the present invention is the same size as the conventionally apparatus without installing sterilizing means therein.

While the present invention has been disclosed in terms of the preferred embodiment in order to facilitate better understanding of the invention, it should be appreciated that the invention can be embodied in various ways without depending from the principle of the invention. Therefore, the invention should be understood to include all possible embodiments and modification to the shown embodiments which can be embodied without departing from the principle of the inventions as set forth in the appended claims.

What is claimed is:

1. An apparatus for dispensing drinking water comprising:
   a chamber in which a container packed with drinking water is mounted;
   conduit means connected with said container in said chamber to dispense drinking water;
   hot water circulating means to circulate hot water through said conduit means; and
   means for determining conditions for achieving sterilization with the hot water of said conduit means;
   wherein said determining means determines said conditions on the basis of the following formula:

$$10^{-((T-55)/5)} \times 5 = t(\min.)$$

wherein $T(° C.)$ is the temperature of said conduit means and T is determined at more than 49° C.; and
   wherein $t(\min)$ is sterilization time passed after temperature of said conduit means reaches T.

2. An apparatus as set forth in claim 1, wherein said conduit means further comprises storage means for storing drinking water within said conduit means.

3. An apparatus as set forth in clam 2, wherein said storage means further comprises two tanks for storing drinking water, one being a cold water tank including refrigeration means to chill the drinking water, the other being a hot water tank including heating means to heat the drinking water.

4. An apparatus as set forth in claim 1, further comprising refrigeration means in said chamber to chill the drinking water in the container.

5. An apparatus as set forth in claim 1, wherein said hot water circulating means includes an automatic control system to automatically control circulation of the hot water.

6. An apparatus for dispensing drinking water comprising:
   a chamber in which a container packed with drinking water is mounted,
   a conduit means connected with said container in said chamber to dispense drinking water,
   sterilizing means installed directly on said conduit means to apply substantial heat thereto, and
   means for determining conditions for achieving sterilization with heat of said conduit means, wherein said determining means determines said conditions on the basis of the following formula:

$$10^{-((T-55)/5)} \times 5 = t(\min.)$$

wherein $T(° C.)$ is the temperature of said conduit means and T is determined at more than 49° C., and
   wherein $(t(\min.)$ is sterilization time passed after temperature of said conduit means reaches T.

7. An apparatus as set forth in claim 6, wherein said conduit means further comprises storage means for storing drinking water within said conduit means.

8. An apparatus as set forth in claim 7, wherein said storage means further comprises two tanks for storing drinking water, one is a chilled water tank including refrigeration means to chill the drinking water, and the other is a heated water tank including heating means to heat the drinking water.

9. An apparatus as set forth in claim 7 further comprising, refrigeration means in said chamber to chill the drinking water in the container.

10. An apparatus as set forth in claim 6, wherein said sterilizing means includes an automatic control system to control automatically, sterilizing with heat.

11. An apparatus as set forth in claim 6, wherein said sterilizing means includes a plurality of heaters.

12. An apparatus as set forth in claim 6, wherein said conduit means has a portion, in which hot water is passed through during dispensing the drinking water, said portion being free of said sterilizing means.

* * * * *